May 30, 1967 S. McGREDY Plant Pat. 2,745
ROSE PLANT
Filed May 2, 1966
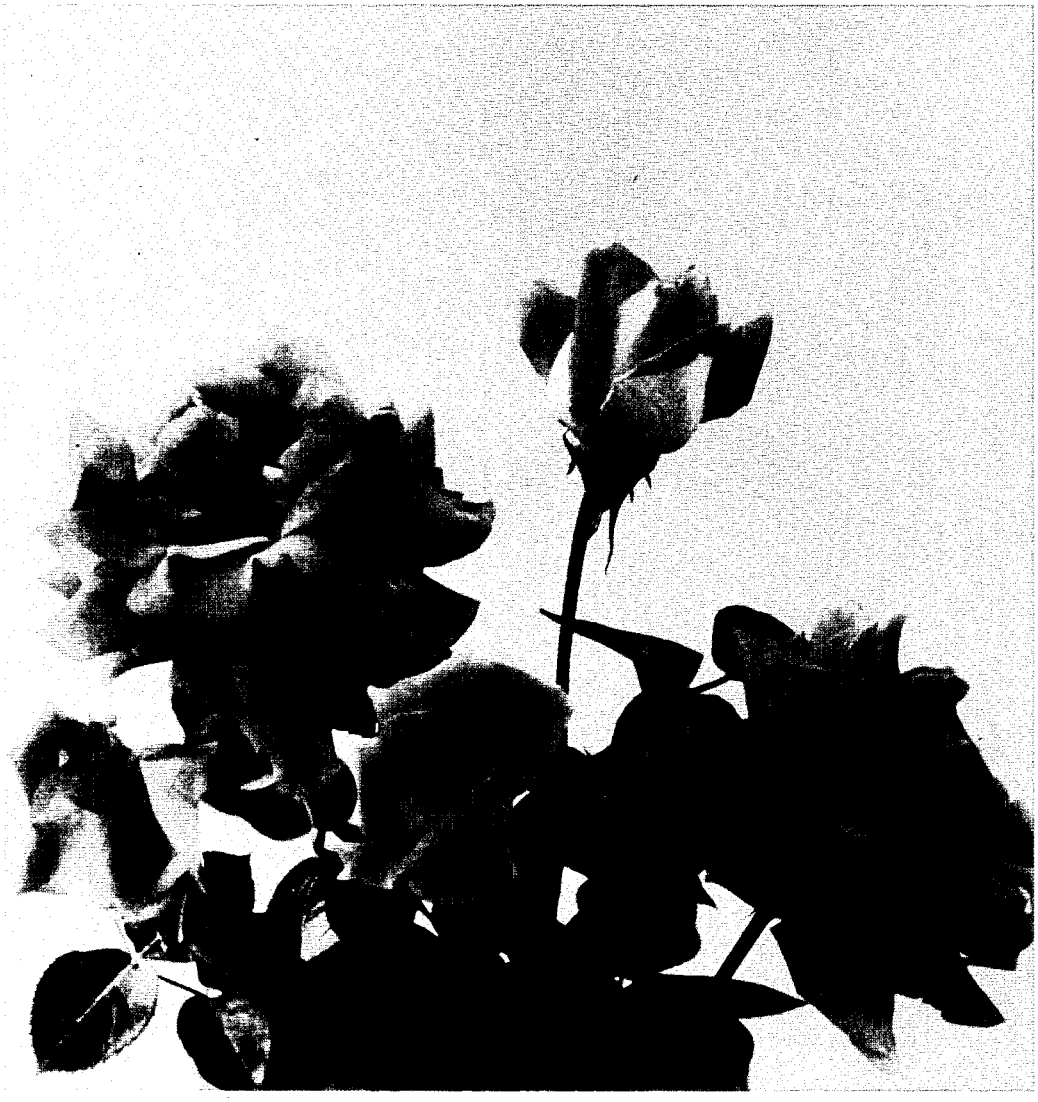

United States Patent Office

Plant Pat. 2,745
Patented May 30, 1967

2,745
ROSE PLANT

Samuel McGredy, % Samuel McGredy & Son Limited, Royal Nurseries, County Armagh, Portadown, Northern Ireland Filed May 2, 1966, Ser. No. 547,113
1 Claim. (Cl. Plt.—12)

The invention relates to a new and distinct variety of rose plant of the hybrid tea class, originated by me, as a consequence of the discovery of a sport in 1960. The parentage of my new rose plant is as follows: Sport of Peace, U.S.A. Plant Patent No. 591.

This sport represents desirable improvements, as evidenced by the following unique combination of characteristics which are outstanding in the new variety and which distinguish it from its parent as well as from all other varieties of which I am aware. My new variety is primarily characterized by a distinct and intensely pigmented bicoloured flower which is deep to medium red on the face of the petals and amber yellow to silver-white on the reverse. The fresh petals are Rose Red (HCC 724–724/3) overlain Beetroot (HCC 830/2) to Dahlia Purple (HCC 931/3). The old petals are Persian Rose (HCC 628/1–628/2) overlain Rose Red (HCC 724/1–724/2). The reverse of the petals is Amber-Yellow (HCC 505–505/3) to silvery-white often flushed and suffused Rose Red (HCC 724/1).

Asexual reproduction of my new variety by budding through a series of annual propagations at Portadown, Northern Ireland, Strasbourg, France, Hemet, Calif., and Livermore, Calif. shows that all characteristics of the variety come true to form through succeeding propagations. The accompanying photographs illustrate the primary characteristics of my new variety as nearly true as is reasonably possible to make them with presently available techniques. The colour references cited are those of the Horticultural Colour Charts of the Royal Horticultural Society.

Having thus disclosed my invention, I claim:

A new and distinct variety of rose plant of the hybrid tea class substantially as herein shown and described primarily characterized by a distinct and intensely pigmented bicoloured flower which is deep to medium red on the face of the petals and amber yellow to silvery-white on the reverse, and which is otherwise similar to the parent variety Peace, Pat. No. 591 of which it is a true sport.

No references cited.

ABRAHAM G. STONE, *Primary Examiner.*

ROBERT E. BAGWILL, *Examiner.*